(12) United States Patent
Petit et al.

(10) Patent No.: US 8,500,780 B2
(45) Date of Patent: Aug. 6, 2013

(54) DYNAMIC LINKING ELEMENT FOR A SPINAL ATTACHMENT SYSTEM, AND SPINAL ATTACHMENT SYSTEM INCLUDING SAID LINKING ELEMENT

(75) Inventors: Dominique Petit, Verton (FR); Thomas Droulout, Chatou (FR)

(73) Assignee: Spinevision (FR)

( * ) Notice: Subject to any disclaimer, the term of this patent is extended or adjusted under 35 U.S.C. 154(b) by 1404 days.

(21) Appl. No.: 10/590,595

(22) PCT Filed: Mar. 2, 2005

(86) PCT No.: PCT/FR2005/000496
§ 371 (c)(1),
(2), (4) Date: Oct. 20, 2006

(87) PCT Pub. No.: WO2005/087121
PCT Pub. Date: Sep. 22, 2005

(65) Prior Publication Data
US 2007/0129729 A1  Jun. 7, 2007

(30) Foreign Application Priority Data
Mar. 2, 2004 (FR) .................................... 04 02150

(51) Int. Cl.
*A61B 17/70* (2006.01)

(52) U.S. Cl.
USPC ............ 606/259; 606/254; 606/261; 606/263

(58) Field of Classification Search
USPC .................. 606/259, 257, 254–255, 261, 263
See application file for complete search history.

(56) References Cited

U.S. PATENT DOCUMENTS

| | | | |
|---|---|---|---|
| 5,704,936 A | 1/1998 | Mazel | |
| 5,725,582 A | 3/1998 | Bevan et al. | |
| 2002/0120270 A1* | 8/2002 | Trieu et al. ...................... | 606/61 |
| 2003/0023241 A1 | 1/2003 | Drewry et al. | |
| 2003/0105459 A1* | 6/2003 | Songer ............................ | 606/61 |
| 2003/0220642 A1* | 11/2003 | Freudiger ....................... | 606/61 |
| 2005/0065516 A1* | 3/2005 | Jahng .............................. | 606/61 |
| 2005/0085814 A1* | 4/2005 | Sherman et al. ................ | 606/61 |

FOREIGN PATENT DOCUMENTS

| | | |
|---|---|---|
| EP | 0 669 109 A1 | 8/1995 |
| FR | 2 799 949 A1 | 4/2001 |
| WO | WO 02/07621 A1 | 1/2002 |

* cited by examiner

*Primary Examiner* — Eduardo C Robert
*Assistant Examiner* — Julianna N Harvey
(74) *Attorney, Agent, or Firm* — DLA Piper LLP (US)

(57) ABSTRACT

A connecting element for a spinal fixing system that connects at least two implantable connection assemblies including a rod including a flexible part extended at one end at least by a rigid part, the flexible part including a cable at least partly surrounded by a polymer envelope, the cable including at least one elastic strand coaxial with the envelope.

17 Claims, 3 Drawing Sheets

DYNAMIC LINKING ELEMENT FOR A SPINAL ATTACHMENT SYSTEM, AND SPINAL ATTACHMENT SYSTEM INCLUDING SAID LINKING ELEMENT

RELATED APPLICATION

This is a §371 of International Application No. PCT/FR2005/000496, with an inter-national filing date of Mar. 2, 2005 (WO 2005/087121 A1, published Sep. 22, 2005), which is based on French Patent Application No. 04/02150, filed Mar. 2, 2004.

TECHNICAL FIELD

The invention relates to the field of spinal fixing systems for connecting vertebrae together, more particularly to the field of connecting elements intended to maintain the spacing between at least two anchoring elements implanted respectively in a vertebra.

BACKGROUND

There exist currently two types of spinal connections: on the one hand osteosynthesis connections and on the other hand dynamic connections.

Spinal osteosynthesis connections are well known connections. They are frequently used to consolidate several consecutive vertebrae. Their purpose is to immobilize the vertebrae connected in a particular configuration and stabilize them during the bone fusion to allow fixed stabilization in the immobilized situation. Such connections consist of rigid rods.

On the other hand, dynamic connections are used to reduce stresses on the articular facets and intervertebral discs by allowing certain movements while, if necessary, realigning the vertebrae with respect to one another.

EP 0 669 109 discloses a device for stabilizing adjoining dorsal vertebrae. That device comprises a connecting element consisting of a band produced from elastic synthetic material and having a round transverse section. The band is intended to be fixed between at least two pedicular screws consisting respectively of a head provided with a transverse piercing. The band is fixed to the pedicular screws by inserting, through the transverse piercing, the band, which is then fixed to each of the pedicular screws by means of a clamping screw disposed along the axis of the corresponding screw, that is to say transversely to the piercing. The device also comprises a support element mounted around the band to form a body resisting pressure.

Such a connecting element does, however, have the drawback of not effecting any torsion return to oppose pivoting movements of the vertebrae around the discs.

Another important drawback of that connecting element is that it cannot be curved so as to adapt to the natural lordosis of the lumbar vertebral column.

In addition, another drawback is that the connecting element occupies a large volume (around 12.5 mm). In some circumstances, it may prove to be difficult to prevent the connecting element in question from coming into contact with the bones, such a contact causing a great deal of pain.

Moreover, such a device has a particularly important drawback relating to the need to choose the length of the support element before fitting the band. It may happen however that the effective distance between the screws after tensioning the band is not exactly that desired. However, the device as configured allows no freedom of relaxation and/or compression between the screws after the fitting of the band and support element. The surgeon therefore has no other choice than to remove the assembly consisting of support element and band in order to introduce a new support element having a different length.

WO 02/07621 discloses a connecting piece intended to maintain the spacing between at least two anchoring elements screwed into vertebrae, the connecting piece comprising: i) a flexible part divided into two continuous branches spaced apart from each other, the branches being substantially symmetrical with respect to the longitudinal axis of the piece, the ends of the branches being connected together in pairs and defining a first mean plane, and ii) two rigid parts forming rods, having a first fixing portion and a second portion, each second portion of the two rigid parts respectively extending in opposite directions from the ends of the branches connected together in pairs, the cross-section of each of the branches being less than the cross-section of the rigid parts so that the connecting piece, whose fixing portions are fixed respectively to each of the two anchoring elements, is able to bend elastically perpendicular to the mean plane during relative movement of the vertebrae, by means of which the vertebrae, kept spaced apart from one another, are able to move with respect to one another.

That connecting piece does, however, have the drawback of being able to bend only in one clearly determined direction, namely perpendicular to the mean plane formed by the two branches. The result is a mounting of the whole of the stabilization system comprising such connecting pieces requiring a certain amount of precision and therefore possibly proving tedious. Another drawback of such a connecting piece is its volume.

SUMMARY

This disclosure relates to a connecting element for a spinal fixing system that connects at least two implantable connection assemblies including a rod including a flexible part extended at one end at least by a rigid part, the flexible part including a cable at least partly surrounded by a polymer envelope, the cable including at least one elastic strand coaxial with the envelope.

BRIEF DESCRIPTION OF THE DRAWINGS

The disclosure will be understood better with the help of the description given below, purely by way of explanation of a selected, representative example, with reference to the accompanying figures.

DETAILED DESCRIPTION

Figure 1:
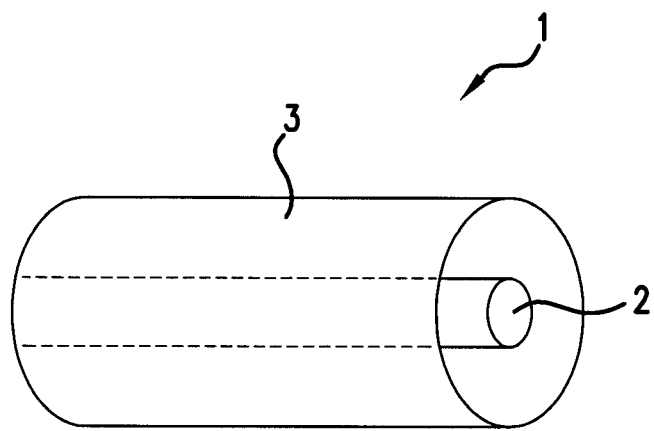
FIG. 1 illustrates a lateral view in perspective of a dynamic connecting element.

We provide a connecting element having an amplitude of flexion equivalent with regard to the dynamic connecting elements, but whose holding in rotation is ensured.

The connecting element also has the advantage of being able to be curved so as to adapt to the natural lordosis of the lumbar vertebral column.

The connecting element also has the advantage of being not very invasive, while providing the functionalities required for a dynamic connecting element (flexibility, resistance to wear, etc).

The connecting element also has the advantage of allowing rapid mounting on the anchoring elements fixed to the vertebrae.

The connecting element has the advantage of being able to undergo relaxation and/or compression after its fitting on the anchoring elements.

To do this, we provide a connecting element for a spinal fixing system intended to connect at least two implantable connection assemblies, the connecting element including a cable and a polymer envelope surrounding the cable, the cable including at least one elastic strand coaxial with the envelope to form the core of the connecting element.

The strand forming the core of the connecting element is defined as the "central strand" for ease of understanding.

Preferably, the connecting element comprises at least one layer of at least six strands distributed around the central strand.

According to one configuration, the connecting element comprises two layers of successive strands disposed around the central strand, the first layer of strands surrounding the central strand consisting of 6 strands, the second layer of strand surrounding the first layer consisting of 12 strands.

Advantageously, the strands constituting the layer or layers include strands twisted around the central strand.

Advantageously, the strands of the layer or layers may be a material different from that of the central strand.

Advantageously, the central strand has a diameter different from that of the strands of the layer or layers. According to the type of configuration required, it may be less than or greater than that of the strands of the layers.

Advantageously, the strands constituting the layer or layers may be titanium or stainless steel.

Advantageously, the central strand is tubular.

Advantageously, the central strand may be made of a nickel-titanium alloy, titanium, stainless steel or polymer, such as for example PEEK or polyurethane.

Advantageously, the envelope is made from polyurethane or PEEK or a biocompatible fabric.

We also provide a connecting element combining the functionalities of a dynamic connecting element with those of an osteosynthesis connecting element. More particularly, the connecting element provides, conjointly with a dynamic connection of at least two vertebrae, the rigid connection of other vertebrae.

This is because, in the case of the fitting of a multilevel vertebrae fixing and stabilization system (instrumentation of several vertebrae) it may prove necessary to connect certain vertebrae together by means of a dynamic connection to allow certain movements, and on the other hand to connect the other vertebrae so that no movement is allowed during bone fusion (osteosynthesis connection). In current fixing and stabilization fixings, the dynamic connecting elements are connected to the rigid connecting elements by means of supplementary fixing elements such as dominoes. The use of supplementary pieces has the drawback of increasing the time for mounting the connecting elements on the anchoring elements.

The disclosed structures therefore relate also to a connecting element for a spinal fixing system, intended to connect at least two implantable connection assemblies comprising a flexible part extended at one of its ends at least by a rigid part, the flexible part comprising a cable at least partly surrounded by a polymer envelope, the cable including at least one elastic strand coaxial with the envelope.

The connecting element thus configured makes it possible to offer dynamic and rigid "connections" for vertebrae without having recourse to supplementary fixing elements.

The connecting element is defined in the remainder of the description as being a "semi-dynamic" connecting element.

Moreover, and the same as previously, in order not to burden the remainder of the description, the elastic strand is referred to as the "central strand".

Preferably, the rigid part has a cavity indented to at least partly receive the cable, the cavity being blind or through.

Advantageously, the cavity is configured to cooperate closely with the cable.

Advantageously, the cavity has a zone widened in the direction of the end receiving the cable.

Advantageously, the flexible part is fixed to the rigid part by adhesive bonding, crimping or welding.

Preferably, the cable comprises at least one layer of 6 strands, the strands being distributed around the central strand. According to one advantageous configuration, the cable comprises two layers of successive strands disposed around the central strand, the first layer of strands surrounding the central strand consisting of 6 strands, the second layer of strands surrounding the first layer consisting of 12 strands.

Advantageously, the strands constituting the layer or layers may be strands twisted around the central strand.

Advantageously, the strands of the layer or layers may be of a material different from that of the central strand.

Advantageously, the central strand has a diameter different from that of the strands of the layer or layers.

Advantageously, the strands constituting the layer or layers may be of titanium or stainless steel or titanium-nickel alloy.

Advantageously, the central strand is tubular.

Advantageously, the central strand may be made of a nickel-titanium alloy, titanium, stainless steel or polymer, such as for example PEEK or polyurethane.

Advantageously, the envelope is made from polyurethane or PEEK or a biocompatible fabric.

Our structures also relate to a spinal fixing system comprising at least two implantable connection assemblies connected by means of at least one or two previously described connecting elements.

Turning now to the Drawings, the connecting elements (1) depicted in FIGS. 1 to 4 constitute dynamic connections as defined above. These connecting elements are intended to connect at least two implantable connection assemblies.

The connecting element (1) illustrated in FIG. 1 consists of a cable (2) surrounded by a relatively flexible envelope (3). The cable (2) for its part consists of an elastic strand or stem.

Strand means a strand consisting either of a single piece ("monostrand") or of several fibres.

Advantageously, the strand is coaxial with the envelope (3) to constitute the central core of the connecting element (1).

Hereinafter, the cable (2) will be referred to as the "central strand", and will also be referenced under the number (2).

The envelope (3) consists of a flexible polymer, such as polyurethane or PEEK (polyetheretherketone). In a particular configuration, the sheath is a biocompatible fabric.

In parallel, in order to offer the necessary return to oppose pivoting movements of the vertebrae around these discs, the cable, when it comprises only a single strand, advantageously consists of a titanium alloy, PEEK, or a superelastic alloy of the nickel/titanium alloy type, also known by the name Nitinol®.

One or more layers of successive strands are disposed around the central strand (2) to improve the characteristic relating to the elasticity of the connecting element.

Figure 2:
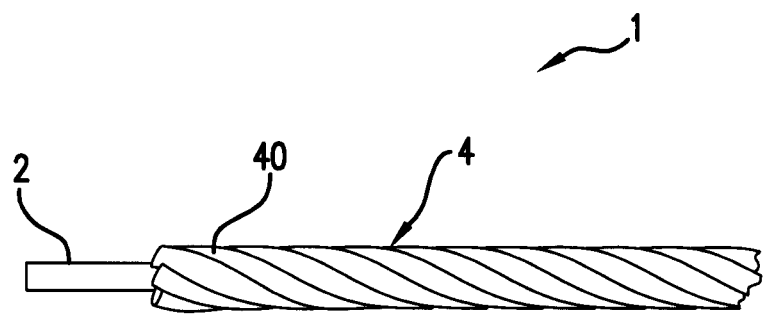
FIG. 2 illustrates another of the connecting elements of FIG. 1.
Figure 3:
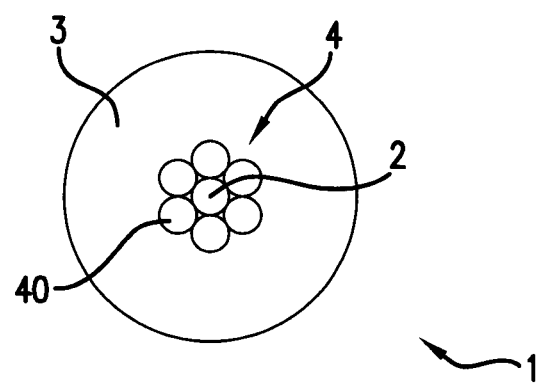
FIG. 3 illustrates a view in section of the connecting element of FIG. 2.

FIGS. 2 and 3 illustrate in particular a connecting element (1) comprising a layer (4) of 6 strands (40) distributed around the central strand (2).

Advantageously, the strands (40) are disposed twisted around the central strand (2).

According to another aspect, the connecting element (1) is characterized in that it comprises a second layer of strands, advantageously consisting of 12 strands, and surrounding the said first layer (4) of 6 strands (40).

These two configurations of layers are here given by way of example. Those skilled in the art know that the organization and number of layers of strands, and the number of strands per layer and their configuration, will depend on the rigidity (or elasticity) required for the connecting element (1).

However, the choice of the form and constitution of the cable is guided by the constraint of the diameter, the purpose being to produce a connecting element with a small diameter (preferably less than or equal to 6 mm) so that the connecting element is as little invasive as possible.

Just like the central strand (2), the strand of each of the layers are made from elastic materials. Advantageously, the strands constituting the third layers and the central strand (2) are formed from titanium, stainless steel or PEEK.

It should be noted, however, that it is not necessary for the strands constituting the layers to be produced from the same material as that from which the central strand (2) is produced.

Likewise, the central strand (2) can also have a form or dimensions different from that of the strands constituting the layers. In particular, the central strand (2) may be in the shape of a tube. In this case, the central strand is preferably made from PEEK, the strands of the layers being made from titanium or stainless steel.

Figure 4:
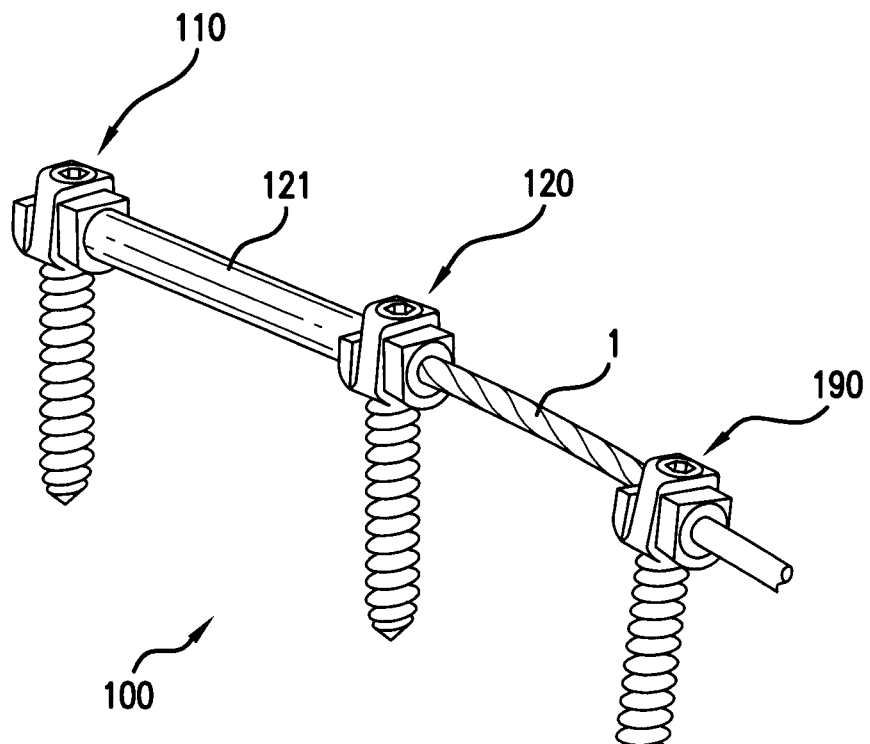
FIG. 4 illustrates a partial view in perspective of a spinal fixing system comprising rigid connecting elements and dynamic connecting elements.

FIG. 4 illustrates a partial view in perspective of a spinal fixing system (100).

The fixing system comprises a plurality of implantable connection assemblies. Only three of these implantable connection assemblies are shown in FIG. 4, these three connection assemblies being respectively referenced 110, 120, 130.

Each connection assembly is respectively connected to an adjoining connection assembly by a connecting element. In particular, in this example, the connection assembly (110) is connected to the connection assembly (120) by means of a spinal osteosynthesis connecting element (121), the connection assembly (120) being connected to the connection assembly (130) by means of a dynamic connecting element (1) according to one of the structures illustrated in FIGS. 1 to 3.

The combination of dynamic connecting elements (1) and spinal osteosynthesis connecting elements (121) thus makes it possible to offer a modular fixing system comprising conventional connecting elements of the osteosynthesis connection type and dynamic connecting elements.

Figure 5:
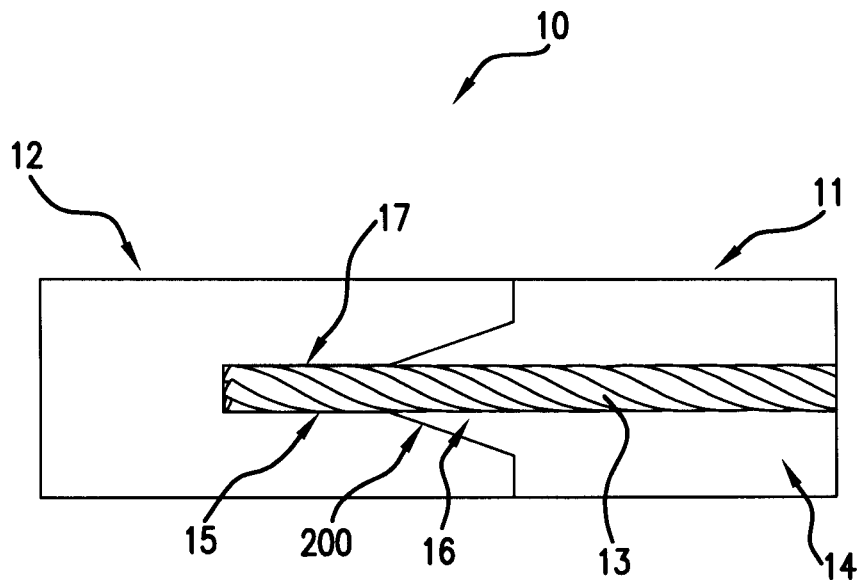
FIG. 5 illustrates a view in section of a semi-dynamic connecting element with a blind cavity.

FIG. 5 illustrates a view in section of a connecting element (10). The connecting element (10) is advantageous in that it constitutes a "semi-dynamic" connection.

The connecting element (10), in the form of a rod, consists of a flexible part (11) and a rigid part (12), the rigid part (12) being fixed in line with the flexible part (11). The "semi-dynamic" behavior of the connecting element (10) is conferred by each of the parts (11, 12), the flexible part (11) fulfilling the role of dynamic connection and the rigid part (12) the role of osteosynthesis connection.

Advantageously, the flexible part (11) consists of a cable (13) at least partly surrounded by a polymer envelope (14), the cable (13) consisting of at least one elastic strand coaxial with the envelope (14). The cable (13) has at one of its ends a bared zone (17) of the envelope (14).

The rigid part (12) has a blind cavity (15) in which the bared zone (17) of the cable (13) is housed. Advantageously, the cavity (15) is configured to permit close cooperation with the cable (13).

Through its constitution and its function, the flexible part (11), and therefore the cable, is regularly subjected to oscillations. However, such a movement generates a risk of shearing of the cable (13).

This is because the cable (13) is bent against the cutting edges formed by the lateral walls of the cavity (15) and the face constituting the end of the rigid part (12). Thus, and to limit this risk of shearing, the cavity (15) has, on the emerging end, a widened zone (16) relative to a narrowed zone (200).

The principle for producing the connecting element (10) is as follows.

The blind cavity (15) is formed longitudinally in the rigid part (12) by piercing. The cable (13) is then introduced into the cavity (15) until it reaches the closed end of the cavity (15). The part of the cable (13) inserted in the cavity (15) is fixed therein by adhesive bonding or crimping. Once the cable (13) is disposed and fixed in the cavity (15) in the rigid part (12), the final step consists of forming the envelope (14) by injecting a polymer around the part of the cable (13) not inserted in the cavity (15).

Figure 6:
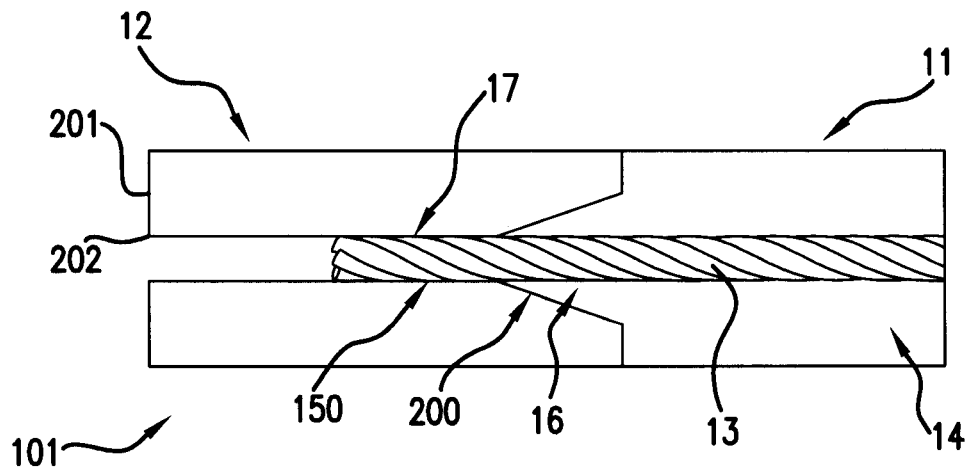
FIG. 6 illustrates a view in section of a semi-dynamic connecting element with a through cavity.

FIG. 6 shows a connecting element (101) that is similar to the connecting element (10) of FIG. 5. However, the connecting element (101) in FIG. 6 has a through cavity (150) that extends from the widened zone (16) to the narrowed zone (200) and to the end (201) of connecting element (101) at opening (202).

Figure 7:
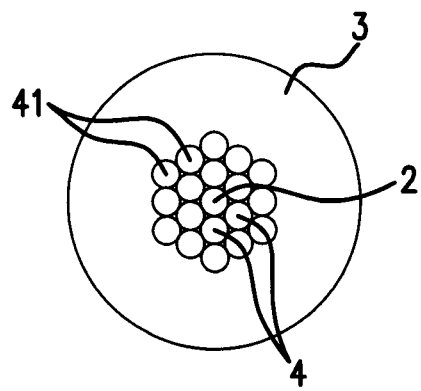
FIG. 7 illustrates a view in section of another connecting element similar to that of FIG. 2 having a second layer of 12 strands.
Figure 8:
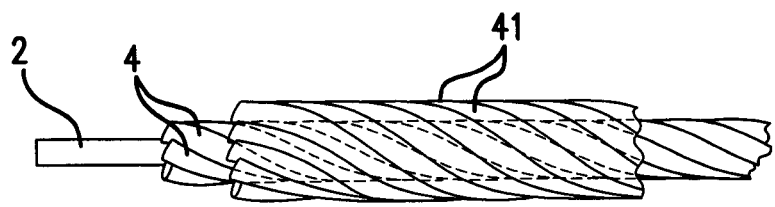
FIG. 8 illustrates a side view of the connecting element of FIG. 7.

FIGS. 7 and 8 show a connecting element that is similar to the connecting element shown in FIGS. 2 and 3 except that there is a second layer (41) comprising 12 strands (40). Second layer (41) is layered over and around layer (4). As indicated in FIG. 8, the strands (40) of second layer (41) are twisted around central strand (22) and strands (40) of first layer (4).

As in the examples described above, the cable (13) consists either of a single elastic strand or an elastic strand surrounded by one or more successive layers of strands, the strands of the layers advantageously being twisted.

Moreover, the description given above relating to the constitution and configuration of the central strand and of the strands in the layers also applies in the context of this configuration.

Moreover, it is naturally evident that the semi-dynamic connecting element (10) is not limited to the configuration illustrated in FIG. 5. This is because it is naturally evident that the flexible part can advantageously be extended on each side by a rigid part.

Likewise, in the case of a multilevel vertebrae fixing and stabilization system, the strand of the flexible part and the rigid part or parts depends on the type of connection required between each adjacent vertebra.

Finally, the dynamic connecting element can advantageously be formed by a plurality of flexible parts separated from one another by a rigid part.

The structures described above are non-limiting examples. One skilled in the art is in a position to implement different variants without departing from the scope of the appended claims.

The invention claimed is:

1. A connecting element for a spinal fixing system that connects at least two implantable connection assemblies comprising: a cable comprising at least one elastic strand at least partly surrounded by and coaxial with a flexible polymer envelope to form a flexible part of the connecting element; and a rigid part having a cavity that at least partly receives the cable, the cavity having a tapered portion with a widened zone proximal to an end receiving the cable and a narrowed zone distal to the end receiving the cable such that the tapered portion of the cavity is filled with a portion of the flexible polymer envelope.

2. The connecting element according to claim 1, wherein the cavity is a through cavity or a blind cavity.

3. The connecting element according to claim 2, wherein the cavity is configured to cooperate with the cable.

4. The connecting element according to claim 1, wherein the flexible part is fixed to the rigid part by adhesive bonding, crimping or welding.

5. The connecting element according to claim 1, wherein the cable comprises at least one layer of at least 6 strands, the strands being distributed around a central strand.

6. The connecting element according to claim 1, wherein the cable comprises two successive layers of strands disposed around a central strand, the first Layer of strands surrounding the central strand comprising 6 strands, the second layer of strands surrounding the first layer comprising 12 strands.

7. The connecting element according to claim 5 or claim 6, wherein the strands constituting the layer or layers comprises strands twisted around the central strand.

8. The connecting element according to claim 5 or claim 6, wherein the strands of the layer or layers are formed from a material different from that of the central strand.

9. The connecting element according to claim 5 or claim 6, wherein the central strand has a diameter different from that of strands of the layer or layers.

10. The connecting element according to claim 5 or claim 6, wherein the strands of the layer or layers are made of titanium or stainless steel, or titanium nickel alloy.

11. The connecting element according to claim 1, wherein the cable comprises a tubular central strand.

12. The connecting element according to claim 1, wherein the cable comprises a central strand formed from an alloy of nickel-titanium, titanium, stainless steel or polymer.

13. The connecting element according to claim 12, wherein the central strand is made from PEEK or polyurethane.

14. The connecting element according to claim 1, wherein the envelope is made from polyurethane.

15. The connecting element according to claim 1, wherein the envelope is made from PEEK.

16. A spinal fixing system comprising at least two implantable connection assemblies connected by at least one connecting element according to claim 1.

17. A connecting element for a spinal fixing system that connects at least two implantable connection assemblies comprising: a cable comprising at least one elastic strand at least partly surrounded by and coaxial with a biocompatible fabric envelope to form a flexible part of the connecting element; and a rigid part having a cavity that at least partly receives the cable, the cavity having a tapered portion with a widened zone proximal to an end receiving the cable and a narrowed zone distal to the end receiving the cable such that the tapered portion of the cavity is filled with a portion of the biocompatible fabric envelope.

* * * * *